United States Patent [19]

Davis

[11] Patent Number: 4,636,562
[45] Date of Patent: Jan. 13, 1987

[54] PROCESS FOR PREPARING 6-HALO-2-CHLOROQUINOXALINE

[75] Inventor: Richard F. Davis, Newark, Del.

[73] Assignee: E. I. Du Pont de Nemours and Company, Wilmington, Del.

[21] Appl. No.: 667,467

[22] Filed: Nov. 1, 1984

Related U.S. Application Data

[63] Continuation-in-part of Ser. No. 375,977, May 7, 1982, abandoned.

[51] Int. Cl.$^4$ .................. C07D 241/44; C07B 1/00
[52] U.S. Cl. ........................... 544/354; 544/356; 564/133
[58] Field of Search ...................... 544/354, 356

[56] References Cited

U.S. PATENT DOCUMENTS 3,252,941 11/1966 Chang et al. ............... 544/354

FOREIGN PATENT DOCUMENTS 48973 3/1982 Japan .

OTHER PUBLICATIONS

Burton et al, J. Chem. Soc. ©1968, pp. 1274–1280.
*BASF*, Chem. Abs., 60, 2987f (1963).
Cheeseman et al, "Condensed Pyrazines", vol. 35, pp. 162, 168 (Wiley, NY) 1979.
A. S. Elina et al., *Zh. Obsch. Khim*, 33, 1544 (1963).
R. E. Lutz et al., *J. Amer. Chem. Soc.*, 68, 1322 (1946).

*Primary Examiner*—Mark L. Berch

[57] ABSTRACT

A process for the preparation of 2-chloro-6-haloquinoxaline compounds from the corresponding 4-halo-2-nitroaniline utilizing four reaction steps with generally compatible solvents and reagents with volatile by-products to minimize the isolation and purification of intermediates has been developed.

10 Claims, No Drawings

PROCESS FOR PREPARING 6-HALO-2-CHLOROQUINOXALINE

RELATED APPLICATION

This application is a continuation-in-part application of Ser. No. 375,977, filed May 7, 1982, abandoned.

TECHNICAL FIELD

This invention relates to a process for the preparation of 6-halo-2-chloroquinoxaline, an important starting material for the synthesis of quinoxalinyloxy ether herbicides.

BACKGROUND OF THE INVENTION

The 6-halo-2-chloroquinoxaline compounds are starting reagents for the preparation of quinoxalinyloxy ether compounds [European Patent Office Application No. 81302801.6, published Dec. 30, 1981] which have utility as herbicides, particularly for the control of grass weeds in paddy rice, soybeans, cotton, potatoes, etc. Rice is the second largest food crop with over 320 million metric tons annual production worldwide [J. R. Harlan, 235 Sci. Amer., 88 (1976)]. Undesired competing vegetation, such as the extremely prevalent barnyardgrass (*Echinochloa crusgalli*) and closely related species can reduce rice yield by 25% if allowed to compete all season at an infestation of only one plant per square foot [Agricultural Age, May 1977, page 11]. Soybeans, with over 60 million metric tons annual production worldwide [Sci. Amer., 235, 88 (1976)] is an extremely valuable crop which must often compete with such grassweeds as crabgrass, barnyardgrass, and wild oats. By inhibiting the growth or killing such undesired vegetation, significant improvements in agricultural efficiency are realized.

Toman et al. [Coll. Czech. Chem. Commun., 43, 2179 (1978)] disclose a procedure for reaction of 4-chloro-2-nitroaniline with diketene in refluxing chlorobenzene at 132° C. The use of such high temperatures results in competing decomposition and polymerization reactions of diketene and a lower yield. Toman et al. also disclose a procedure for reaction of 4-chloro-2-nitroacetoacetanilide with base in aqueous ethanol to produce the 2-hydroxyquinoxaline-4-oxide. The use of ethanol-water solvent is costly, precludes direct continued use of the reaction product in subsequent processing steps and results in waste streams containing flammable materials.

U.S. Pat. No. 3,708,580 discloses the reaction of substituted 2-nitroanilines with diketene in a solution of glacial acetic acid and mercuric acetate. Continued processing of the 2-nitroacetoacetanilide requires additional separation steps. Also disclosed is the reaction of substituted 2-nitroacetoacetanilides with 18% potassium hydroxide.

Lacey [J. Chem. Soc., 850 (1954)] discloses the use of triethylamine as a catalyst for reactions of diketene with alkoxycarbonyl-amines to produce derivatives of acetoacetamide. The aromatic amine compounds studied do not, however, include either nitro- or halogen substitution, which as electron withdrawing substituents, reduce the basicity of the amine group. Such reduced basicity is stated by Lacey to result in sluggish reaction.

Tennant [J. Chem. Soc., 1963, 2428] describes the synthesis of unsubstituted 2-hydroxyquinoxaline-4-oxide, and also its reduction with sodium dithionite in acetic acid to produce 2-quinoxalinol. The yield was not reported, and the reduction of compounds with halogen substitution at the six (6)-position was not considered.

Amad et al. [Tetrahedron 20, 1107 (1964)] reports the use of sodium dithionite to reduce 6-chloro-3-cyano-2-hydroxyquinoxaline-4-oxide. The reaction results in the loss of the nitrile group (strongly electron withdrawing) with simultaneous formation of 2-hydroxyquinoxaline.

Katritzky and Monro [J. Chem. Soc., 1958, 1263] describe the reduction of substituted pyridine N-oxides using hydrogen and palladium/carbon catalyst. The substituted fused-ring quinoline 4-oxides are however reported to be resistant to such reduction.

Taylor and Jefford [Chem. and Ind., 1963, 1559] disclose the reduction of quinoxaline-4-oxides with amino substitution to block the reactive three (3)-position using hydrogen and Raney nickel catalyst. The reaction is run in a mixture of ethanol and methylamine, and the effect of halogen substitution in the aromatic ring is not considered.

Crowther et al. [J. Chem. Soc., 1949, 1260] discloses the use of phosphorus oxychloride for the conversion of 2-hydroxyquinoxalines to 2-chloroquinoxalines. The phosphorous compound by-products are removed by reacting with ice-water to decompose them to an aqueous phosphoric acid solution.

Given the anticipated importance of quinoxalinyloxy ether herbicides, what is needed is an economical process for producing 6-halo-2-chloroquinoxaline compounds at high yield without contamination by isomeric impurities.

SUMMARY OF THE INVENTION

By specifically designing the reaction steps of the instant process invention to utilize compatible solvents and reagents with volatile by-products, it has been found possible to produce 2-chloro-6-haloquinoxaline from 4-halo-2-nitroaniline in good yield, with minimum isolation, and no purification, of process intermediates. By insuring maximum interconnection of the process steps, handling losses are minimized resulting in high overall yield. The instant invention also avoids the production of 7-halo isomer compounds. Specifically, one aspect of this invention involves the preparation of 2-chloro-6-haloquinoxaline, wherein the halo-substituent can be fluorine, chlorine, or bromine, by the process comprising (a) contacting, and reacting 4-halo-2-nitroaniline with diketene to produce 4-halo-2-nitroacetoacetanilide followed by removing solvent therefrom to enable subsequent processing; (b) contacting and reacting 4-halo-2-nitroacetoacetanilide with aqueous alkali metal hydroxide to produce 6-halo-2-hydroxyquinoxaline-4-oxide followed by dilution of the reaction mass to a suitable alkali metal hydroxide concentration for subsequent processing; (c) contacting and reacting 6-halo-2-hydroxyquinoxaline-4-oxide with hydrogen to produce 6-halo-2-quinoxalinol which is separated from the reaction mass and dried for subsequent processing; and (d) contacting and reacting the 6-halo-2-quinoxalinol with acid chloride to produce 2-chloro-6-haloquinoxaline. Another aspect of this invention comprises the processes embodied by the individual steps (a), (b), (c), or (d) described above with their associated preferred conditions. Recovery of the products of the individual process steps is by conventional separation or purification techniques.

DETAILED DESCRIPTION OF THE INVENTION

The process of this invention for preparing 2-chloro-6-haloquinoxaline compounds is exemplified by the reactions of Equations 1–4. As shown in Equation 1, wherein X is chlorine, fluorine, or bromine,

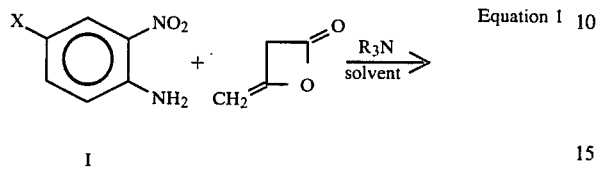

Equation 1

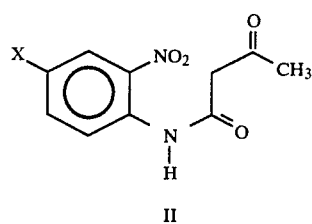

II the first step of the process involves reacting compound I (4-halo-2-nitroaniline) with diketene to produce the corresponding substituted 4-halo-2-nitroacetoacetanilide, compound II. This is conveniently carried out by contacting compound I with a 10% by weight excess of diketene in the presence of a catalytic amount of a non-nucleophilic amine, such as 1,4-diazabicyclo[2.2.2]octane (DABCO) or other trisubstituted aliphatic amine. The substituents on the trisubstituted aliphatic amine catalyst are $C_1$–$C_4$ alkyl, preferably triethyl, and the catalyst selected can be used in the 0.1–10% by weight concentration range, preferably 1–3% by weight.

The reaction of Equation 1 is best carried out in inert organic solvent, preferably aromatic. Benzene or toluene is preferred since their relatively low boiling points enable good thermal control of the reaction by reflux at temperatures which avoid decomposition or polymerization of diketene. The aniline of Formula I, wherein X is as previously defined, and the desired catalyst are dissolved in the organic solvent and heated to a temperature in the range 50°–115° C., with 80°–110° being preferred. Diketene, in a small volume of the organic solvent, is slowly added to compound I while maintaining the desired temperature. After addition is complete, the temperature is maintained for 0.5–12 hours, preferably 2–4 hours.

The reaction of Equation 1 can preferably be carried out by the following procedure: A solution of the aniline of compound I and 2% by weight triethylamine in benzene or toluene is heated at reflux and a solution of 1.1 equivalent of diketene in an equal volume of the same solvent is slowly added. Reflux is maintained for 2 hours, followed by cooling of the solution to room temperature. The solvent, excess diketene, and triethylamine are removed under vacuum leaving the solid product, compound II.

The 2-hydroxyquinoxaline-4-oxide compounds of Formula III are prepared by reacting the product of Equation 1, compound II with alkali metal hydroxide as shown in Equation 2.

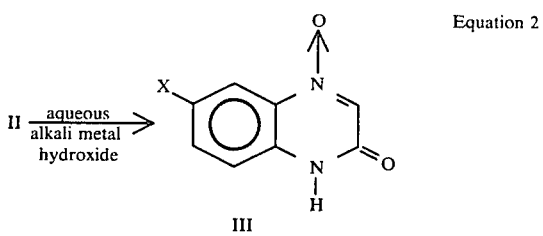

Equation 2

III

The reaction depicted by Equation 2 is carried out by heating compound III in aqueous 3–20% by weight alkali metal hydroxide, preferably potassium hydroxide or sodium hydroxide at 5–10% by weight concentration, to a temperature of from 70°–90° C., preferably 80° C., for 0.5 to 3 hours.

The reaction of Equation 2, the second step of the process invention, is preferably carried out by the following procedure: Solid compound II, either crude or recrystallized if desired, is added to an aqueous solution containing at least 4 equivalents of sodium hydroxide or potassium hydroxide. Four equivalents or more of base are employed in this step to ensure the presence of at least 3 equivalents for the subsequent reduction step; one equivalent is consumed in the cyclization. The mixture is heated to the desired reaction temperature for 1 hour, and then cooled to room temperature. The mixture is then diluted with water to produce the requisite base concentration for direct, continued processing in the third reaction step, or alternatively is acidified to precipitate solid compound III which can be filtered, washed with water, and dried under vacuum.

The third step of the process involves the conversion of compound III to the corresponding 6-halo-2-quinoxalinol of Formula IV by contacting with hydrogen in the presence of a catalyst as shown in Equation 3.

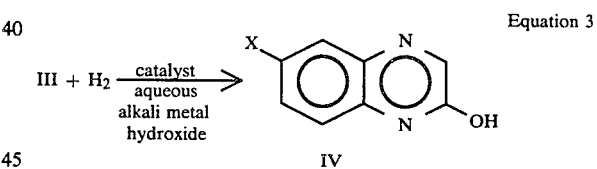

Equation 3

IV

The solvent for the reaction is aqueous 2–10% by weight alkali metal hydroxide, preferably about 2–5% by weight sodium hydroxide or potassium hydroxide. At least three equivalents of base are required to solubilize III, and minimize both the reaction time and formation of side-products. The reaction temperature can be 15°–50° C., but is preferably maintained in the range 20°–35° C. Hydrogen pressures of 1–4 atmospheres are effective, with 1–2 atmospheres preferred. The hydrogenation catalyst is an active form of a transition element metal such as platinum, rhodium, nickel, ruthenium, cobalt, or copper in an inactive support or in some other standard form. The preferred catalyst is Raney Nickel with a range of reaction times of 0.5–5 hours, preferably 1–2 hours.

The reaction of Equation 3 is preferably carried out by the following procedure: The solution of compound III in 5% by weight alkali metal hydroxide resulting from the second step of the process, or solid compound III dissolved in 5% by weight alkali metal hydroxide, is rapidly stirred at room temperature while adding a portion of Raney Nickel catalyst. A fine stream of hydrogen is continuously passed through the solution for 1-2 hours. The mixture is then flushed with nitrogen and the catalyst filtered out. The resulting solution is then acidified and the precipitated compound IV filtered out, washed with water, and dried under vacuum. Alternatively the wet filter cake is resuspended in an aromatic organic solvent and the water removed by azeotropic distillation.

The fourth step of the process, the conversion of compound IV to the corresponding 2-chloro quinoxaline compound of Formula V is shown in Equation 4.

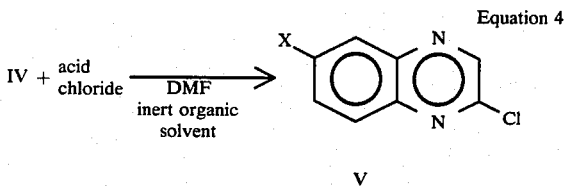

Equation 4

Reaction of compound IV with an inorganic acid chloride such as thionyl chloride or phosphorous oxychloride, or with phosgene dissolved in a suitable aromatic organic solvent containing a catalytic amount of dimethylformamide (DMF) results in the formation of compound V. Thionyl chloride and phosgene are the preferred chlorination reagents since unreacted material and reaction by-products are volatile and easily removed from the final product. The organic solvent can be any suitable aromatic solvent such as benzene, toluene, xylene, or monochlorobenzene with toluene preferred. Reaction occurs in the range 80°-120° C., preferably 90°-110° C., with reaction times of 1-4 hours, preferably 2-3 hours. The acid chloride is slowly added to the suspension of compound IV at the desired temperature with completion of the reaction indicated by the cessation of gas evolution.

The reaction of Equation 4 is preferably carried out by the following procedure: A suspension of compound IV in a suitable solvent contaning a catalytic amount of DMF is heated to about 100° C. and 2-3 equivalents of thionyl chloride is slowly added while maintaining the temperature. Alternatively, phosgene can be introduced as a gas and condensed into the reaction mixture using a condenser cooled to −78° C. The mixture is heated at the desired temperature for 2-3 hours until gas evolution ceases, and is then cooled. Excess acid chloride is distilled out of the resulting mixture or neutralized with dilute base, and any insoluble material removed by filtration. The resulting solution is washed with dilute base, dried, and evaporated to give a solid, 2-chloro-6-haloquinoxaline. If desired, the product can be recrystallized from solvents such as ethyl acetate.

EXAMPLES

Unless specified otherwise, in all statements of process conditions, temperature is expressed in °C. with a ±2° C. experimental limit of error, and concentrations referred to as percentages (%) are by weight.

EXAMPLE 1

A solution of 34 gm (0.2 mole) of 4-chloro-2-nitroaniline and 1 ml of triethylamine in 330 ml of benzene was heated at reflux and 17.7 ml (0.22 mole) of diketene in 20 ml benzene was added dropwise over 20-30 minutes. The mixture was then heated at reflux for 4 hours. After cooling to room temperature, the benzene was removed on a rotary evaporator and the product recovered. The product as isolated was 53 gm of light brown solid. This material was recrystallized from 150 ml of ethanol. The first crop provided 40 gm of yellow crystalline solid, 4-chloro-2-nitro-acetoacetanilide, melting point (m.p.) 77°-81°.

nmr (CDCl$_3$)δ: 8.7 (1H, d, J=9); 8.2 (1H, d, J=2); 7.6 (1H, d of d, J=9,2); 3.7 (s, ~2H); and 2.37 (s, ~3H).

ir (nujol): 3350, 1650, 1620, 1570, 1510, 1340, 1270, 1240, 1225, 1170, 1150, 900, 800, 730 cm$^{-1}$.

mass spectrum: m/e 256 (1×Cl).

EXAMPLE 2

50 gm of 4-chloro-2-nitroacetoacetanilide (from Example 1) was dissolved in 500 ml of 6.5% aqueous sodium hydroxide. The mixture was heated at 80° C. for 0.5 hour, then cooled to room temperature and diluted with 1500 ml water. Insoluble 4-chloro-2-nitroaniline was filtered out, and the filtrate was acidified with HCl. The precipitated product was filtered out, washed with water and dried in a vacuum oven.

The product as isolated was 31 gm of light reddish brown solid, 6-chloro-2-hydroxyquinoxaline-4-oxide.

ir (nujol): 1690, 1520, 1270, 1260, 1150, 1130, 850, 830 cm$^{-1}$.

mass spectrum: m/e 196 (1×Cl).

EXAMPLE 3

3 gm of 6-Chloro-2-hydroxyquinoxaline-4-oxide from Example 2 was dissolved in 300 ml of 5% NaOH at room temperature. A small amount of insoluble solid was filtered out, and the solution was put in a gas washing bottle with a sintered glass frit on the inlet tube. Approximately 4-5 grams of Raney Nickel catalyst was added, and a stream of hydrogen was bubbled through the solution while it was stirred vigorously at room temperature. After 1 hour the system was flushed with nitrogen, the catalyst was filtered out and the filtrate was acidified with 3N HCl. The precipitate was filtered, washed with water and dried under vacuum to recover the product. The product as isolated was 1.7 gm of lavender colored solid, 6-chloro-2-hydroxyquinoxaline, m.p. >250°.

ir (nujol): 1690, 1645, 1410, 1265, 1235, 1185, 1130, 1070, 970, 930, 890, 815, 735 cm$^{-1}$.

mass spectrum: m/e 180 (1×Cl).

EXAMPLE 4

1.7 gm of 6-chloro-2-hydroxyquinoxaline (from Example 3) was added to 0.1 ml DMF (dimethylformamide) and 25 ml of toluene. The mixture was heated to 100° and 2.5 ml of thionyl chloride was added. The mixture was heated at 100° for ~1 hour until gas evolution ceased. It was cooled, poured into 20 ml of 5% NaOH and the toluene layer separated, washed with saturated NaCl solution, and dried using a rotary evaporator to recover the product. The product as isolated was 1.4 gm of tan crystalline solid, 2,6-dichloroquinoxaline, m.p. 142°-145°. Recrystallized product has m.p. 154°-155°.

nmr (CDCl$_3$)δ: 8.85 (s, 1H); 8.2 (t, J=2, 1H); 8.0 (s, 1H); and 7.85 and 7.75 (2 d's, J=2, 1H).

ir (nujol): 3040, 1600, 1545, 1270, 1245, 1150, 1090, 1070, 1000, 960, 920, 895, 840 cm$^{-1}$.

EXAMPLE 5

A solution was prepared by dissolving 34 gm of 4-chloro-2-nitroaniline and 1 ml of triethylamine in 330 ml of benzene. While heating the solution at reflux, 17 ml of diketene in 20 ml benzene was added dropwise. The reaction mixture was heated at reflux for 2 hours, cooled at room temperature and the benzene removed on a rotary evaporator.

The yellow solid residue was dissolved in 500 ml of 20% aqueous KOH and heated at 80° for 1 hour. The solution was then cooled, diluted with 1500 ml water and a small amount of insoluble solid was filtered out.

The filtrate was stirred at room temperature in a 5 liter flask, 15 gm of Raney Nickel catalyst was added, and a stream of hydrogen was bubbled through the mixture for 1 hour using a fritted glass gas dispersion tube. The system was flushed with nitrogen, the catalyst filtered out and the filtrate acidified with HCl. The solid precipitate was filtered, washed with water and pulled as dry as possible in the funnel.

The solid wet cake was added to 1200 ml of toluene and the mixture heated at reflux while all of the water was azeotroped out. When the reflux temperature reached 110° and no more water was coming over, the temperature was dropped to 100°, 2 ml of DMF was added, and 40 ml of thionyl chloride was added dropwise. After the addition was complete, the mixture was heated at 100° until gas evolution ceased (2.5 hours). The solution was cooled, poured into 1 liter of 5% NaOH, and insoluble solid filtered out. The toluene layer was separated, washed with saturated aqueous sodium chloride, dried and the solvent removed to recover the product.

The product as isolated was 22.6 gm of tan solid, 2,6-dichloroquinoxaline, m.p. 148°–152°. NMR was the same as product from Example 4, HPLC analysis showed 97% purity.

Substantially the same procedures as in Examples 1–5 can be used to synthesize 6-fluoro- or 6-bromo-derivatives of 2-chloroquinoxaline.

It will be apparent that the instant specification and examples are set forth by way of illustration and not limitation, and that various modifications and changes may be made without departing from the spirit and scope of the present invention.

What is claimed is:

1. A process for preparing a 6-halo-2-quinoxalinol compound of the formula:

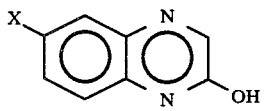

wherein X is F, Cl, or Br, comprising reacting 6-halo-2-hydroxyquinoxaline-4-oxide with hydrogen in the presence of a transition element metal catalyst selected from the group consisting of platinum, rhodium, nickel, ruthenium, cobalt, and copper in an aqueous solution containing at least three equivalents of alkali metal hydroxide thereby producing the 6-halo-2-quinoxalinol compound.

2. The process of claim 1 wherein said reaction is carried out at a pressure of 1 to 4 atmospheres and a temperature of from about 15° to 50° C. for a time period of at least 0.5 hours.

3. The process of claim 2 wherein the transition element metal catalyst is Raney nickel and the alkali metal hydroxide is sodium hydroxide or potassium hydroxide.

4. The process of claim 3 wherein X is Cl.

5. The process of claim 4 wherein said reaction is carried out at a pressure of 1 to 2 atmospheres and a temperature of from about 20° C. to 35° C. for a time period of from 0.5 to 5 hours.

6. A process for preparing a 2-chloro-6-haloquinoxaline compound of the formula:

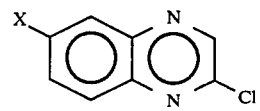

wherein
X is F, Cl or Br, comprising: (a) reacting 4-halo-2-nitroaniline with diketene in the presence of a non-nucleophilic amine catalyst to produce 4-halo-2-nitroacetoacetanilide; (b) forming a reaction mixture comprising the 4-halo-2-nitroacetoacetanilide in an aqueous solution containing at least 4 equivalents of alkali metal hydroxide to produce 6-halo-2-hydroxyquinoxaline-4-oxide followed by dilution of the reaction mixture to yield in step (c) an alkali metal hydroxide concentration of about 2% to about 10% by weight; (c) reacting said reaction mixture with hydrogen in the presence of a transition element metal catalyst selected from the group consisting of platinum, rhodium, nickel, ruthenium, cobalt, and copper in aqueous alkali metal hydroxide solvent, thereby producing 6-halo-2-quinoxalinol; and (d) contacting the 6-halo-2-quinoxalinol with an acid chloride, thereby producing said 2-chloro-6-haloquinoxaline compound.

7. The process of claim 6 wherein said reaction in step (c) is carried out at a pressure of 1 to 4 atmospheres and a temperature of from about 15° C. to 50° C. for a time of at least 0.5 hours.

8. The process of claim 7 wherein the transition element metal catalyst is Raney nickel and the alkali metal hydroxide is sodium hydroxide or potassium hydroxide.

9. The process of claim 8 wherein X is Cl.

10. The process of claim 9 wherein said reaction in step (c) is carried out at a pressure of 1 to 2 atmospheres and a temperature of from about 20° C. to 35° C. for a time period of from 0.5 to 5 hours.

* * * * *